(12) United States Patent  
Harley et al.

(10) Patent No.: US 9,390,884 B2  
(45) Date of Patent: Jul. 12, 2016

(54) METHOD OF INSPECTING A SEMICONDUCTOR SUBSTRATE

(71) Applicant: GLOBALFOUNDRIES INC., Grand Cayman (KY)

(72) Inventors: Eric C. Harley, Lagrangeville, NY (US); Oliver D. Patterson, Poughkeepsie, NY (US); Kevin T. Wu, Hopewell Junction, NY (US)

(73) Assignee: GLOBALFOUNDRIES INC., Grand Cayman (KY)

( * ) Notice: Subject to any disclaimer, the term of this patent is extended or adjusted under 35 U.S.C. 154(b) by 96 days.

(21) Appl. No.: 14/274,042

(22) Filed: May 9, 2014

(65) Prior Publication Data

US 2015/0325406 A1     Nov. 12, 2015

(51) Int. Cl.
| | | |
|---|---|---|
| *H01L 21/00* | (2006.01) |
| *H01J 37/22* | (2006.01) |
| *H01J 37/244* | (2006.01) |
| *G01N 23/225* | (2006.01) |
| *G01B 15/02* | (2006.01) |

(52) U.S. Cl.
CPC .............. *H01J 37/222* (2013.01); *G01B 15/02* (2013.01); *G01N 23/2251* (2013.01); *H01J 37/244* (2013.01); *H01J 2237/063* (2013.01); *H01J 2237/221* (2013.01); *H01J 2237/24592* (2013.01)

(58) Field of Classification Search
CPC ... H01L 21/00; H01L 31/1884; H01L 31/074; H01J 37/28
USPC ..................................... 438/85; 250/306, 310
See application file for complete search history.

(56) References Cited

U.S. PATENT DOCUMENTS

| | | | |
|---|---|---|---|
| 6,895,109 B1 | 5/2005 | Schemmel et al. |
| 6,925,202 B2 | 8/2005 | Karklin et al. |
| 7,646,908 B2 | 1/2010 | Onishi |
| 7,689,967 B2 | 3/2010 | Pang |
| 7,734,082 B2 | 6/2010 | Honda et al. |
| 7,835,565 B2 | 11/2010 | Cai et al. |
| 7,843,559 B2 | 11/2010 | Furman et al. |
| 8,260,032 B2 | 9/2012 | Preil et al. |
| 8,358,831 B2 | 1/2013 | Doe et al. |
| 2004/0113073 A1* | 6/2004 | Nakasuji et al. ............. 250/306 |
| 2005/0194535 A1* | 9/2005 | Noji et al. ..................... 250/311 |
| 2007/0196769 A1* | 8/2007 | Kang et al. ................... 430/296 |
| 2012/0307043 A1 | 12/2012 | Akiyama et al. |
| 2013/0094752 A1 | 4/2013 | Tsuchiya et al. |
| 2014/0306109 A1* | 10/2014 | Sun et al. ...................... 250/307 |

FOREIGN PATENT DOCUMENTS

| | | |
|---|---|---|
| EP | 0628923 A2 | 12/1994 |
| WO | 0140770 A2 | 6/2001 |
| WO | 2012148848 A2 | 11/2012 |

* cited by examiner

*Primary Examiner* — Phuc Dang  
(74) *Attorney, Agent, or Firm* — Catherine Ivers, Esq.

(57) ABSTRACT

A semiconductor substrate inspection system includes an e-beam inspection system configured to deliver electrons to a specimen semiconductor substrate. A sensor is configured to detect reflected electrons that reflect off the surface of the specimen semiconductor substrate. An analysis unit is configured to determine a number of electrons received by the semiconductor substrate, and to determine at least one target region including at least one defect of the semiconductor substrate. A reference image module is in electrical communication with the analysis unit. The reference image module is configured to generate a first digital image having a plurality of pixels, and to adjust a gray-scale level of the pixels included in the target region based on the number electrons included in each pixel to generate a second digital image that excludes the at least one defect.

7 Claims, 13 Drawing Sheets

METHOD OF INSPECTING A SEMICONDUCTOR SUBSTRATE

BACKGROUND

The present invention relates to semiconductor inspection systems, and more specifically, to an e-beam semiconductor inspection system configured to detect defects in a fabricated semiconductor circuit.

SUMMARY

According to at least one embodiment a method of inspecting a semiconductor substrate comprises delivering a beam of electrons to the semiconductor substrate and generating a first image having a plurality of pixels based on electrons emitted from the semiconductor substrate. The method further includes determining a number of electrons emitted by the semiconductor substrate. The method further includes determining at least one target region including at least one defect of the semiconductor substrate. The method further includes adjusting a gray-scale level of the pixels included in the target region based on the number of received electrons to generate a second image that excludes the at least one defect.

A semiconductor substrate inspection system includes an e-beam inspection system configured to deliver electrons to a specimen semiconductor substrate. A sensor is configured to detect reflected electrons that reflect off the surface of the specimen semiconductor substrate. An analysis unit is configured to determine a number of electrons received by the semiconductor substrate, and to determine at least one target region including at least one defect of the semiconductor substrate. A reference image module is in electrical communication with the analysis unit. The reference image module is configured to generate a first digital image having a plurality of pixels, and to adjust a gray-scale level of the pixels included in the target region based on the number electrons included in each pixel to generate a second digital image that excludes the at least one defect.

Additional features are realized through the techniques of the present invention. Other embodiments are described in detail herein and are considered a part of the claimed invention. For a better understanding of the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing features are apparent from the following detailed description taken in conjunction with the accompanying drawings in which:

DETAILED DESCRIPTION

Figure 1:
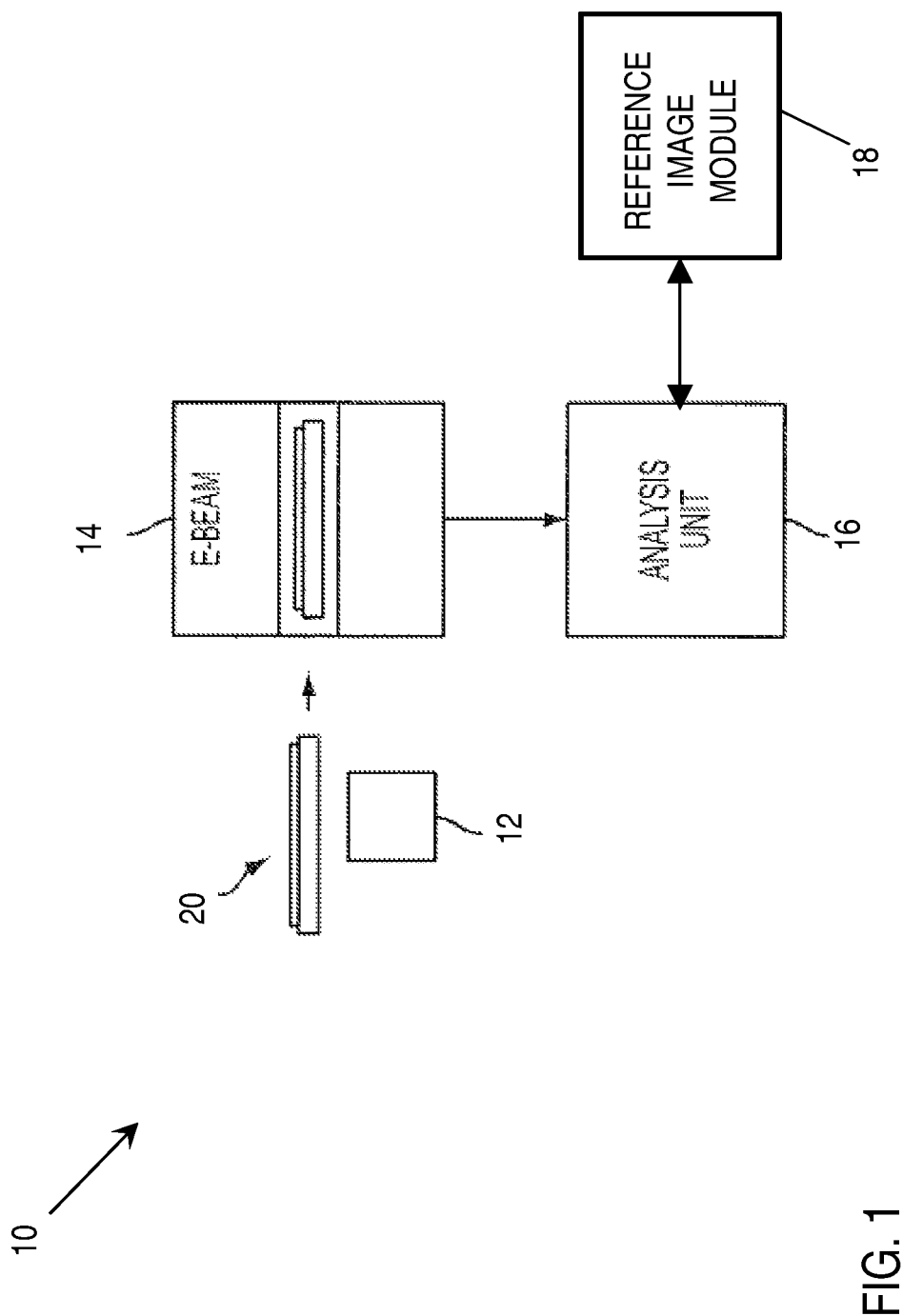
FIG. 1 is a block diagram of a semiconductor inspection system according to at least one exemplary embodiment.

With reference to FIG. 1, a semiconductor inspection system 10 is illustrated according to at least one exemplary embodiment. The semiconductor inspection system 10 includes a conveyor apparatus 12, an e-beam inspection unit 14, an electronic analysis unit 16, and a reference image module 18. The conveyer apparatus 12 may support one or more semiconductor substrates 20 disposed therein and may deliver the semiconductor substrates 20 to the e-beam inspection unit 14. The semiconductor substrate 20 may include one or more finFET devices having a plurality of semiconductor fins and an epitaxial grown material (epi) that merges the fins together. The epi may include one or more defects that may be detected by the e-beam inspection unit 14. The defects may include, but are not limited to, partially grown epitaxial regions located between a pair of fins. Although a semiconductor substrate 20 including finFET semiconductor devices are described going forward, it is appreciated that the semiconductor substrate 20 may include various types of semiconductor devices such as, for example, a CMOS device, conventional planar field effect transistor (FET) device, and a nanowire FET device and the semiconductor substrate 20 may be at various stages of processing, such as after epitaxial grown of fins, etch of the gate trenches, CMP of the gates and CMP of the contacts.

Figure 2:
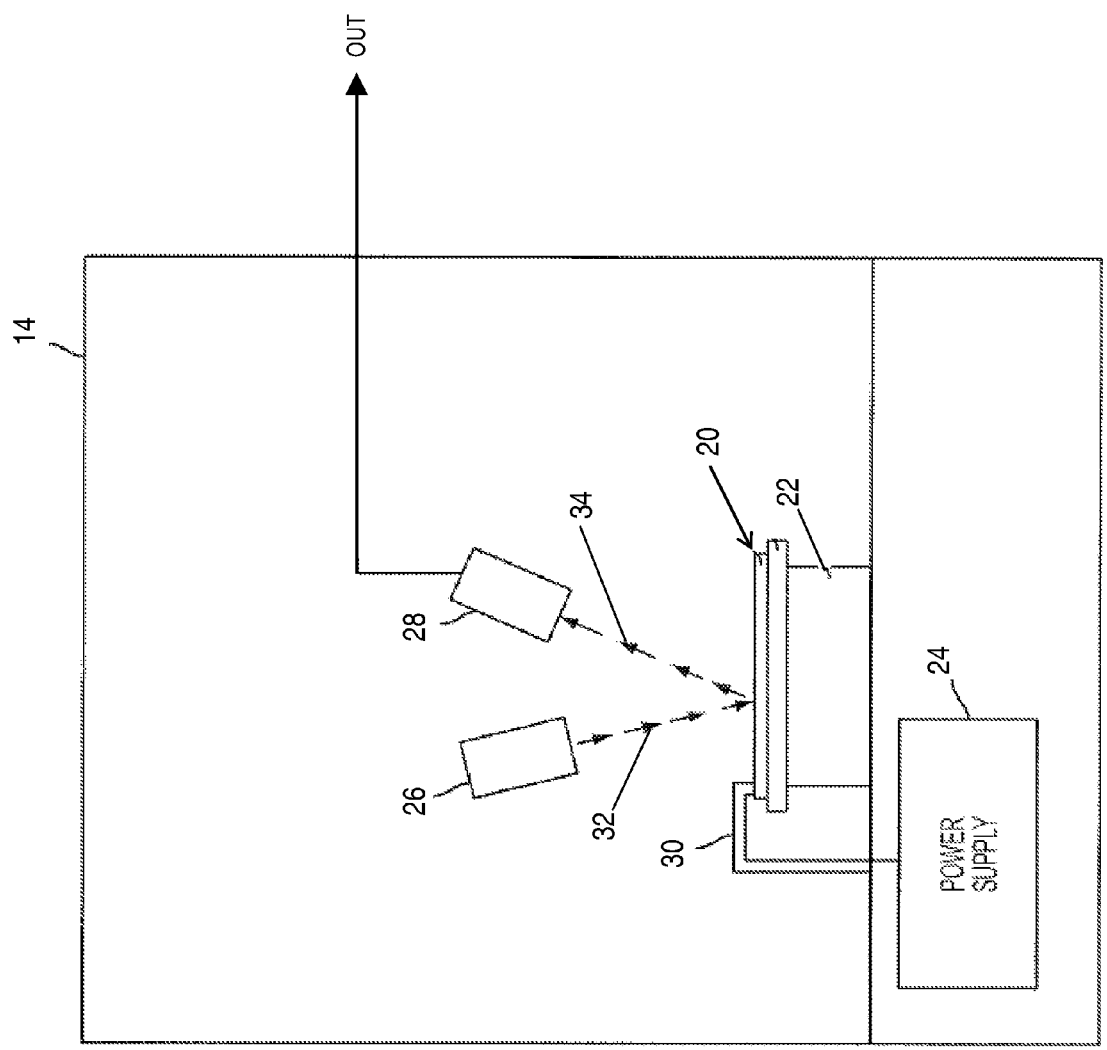
FIG. 2 is a block diagram of an e-beam inspection unit according to at least one exemplary embodiment.

The e-beam inspection unit 14 is configured to detect one or more defect types corresponding to a specimen semiconductor substrate 20 received from the conveyer 12. Referring to FIG. 2, for example, the e-beam inspection unit 14 includes, for example, a substrate stage 22, one or more a power supplies 24, an e-beam generating device 26, a sensor 28, and an electronic image processor 30. The substrate stage 22 may move and position the semiconductor substrate 20 in an analysis position with respect to the e-beam generating device 26.

The power supply 24 includes an electrically conductive lead 30 connected to the semiconductor substrate 20. In this regard, the power supply 24 generates power that energizes the semiconductor substrate 20. The energized semiconductor substrate 20 promotes the electrons of the e-beam to travel toward the semiconductor substrate 20. Although a power supply 24 connected to the semiconductor substrate 20 is illustrated, other means of energizing the semiconductor substrate 20 may be used as understood by those ordinarily skilled in the art. For example, a laser beam generator may be provided that delivers charged particles to the semiconductor substrate 20, thereby energizing the substrate 20.

The e-beam generating device 26 is configured to move the electron beam with respect to the substrate stage 22 and may generate an e-beam 32 (including electrons) that is directed toward the semiconductor substrate 20. The e-beam 32 impinges the semiconductor substrate 20, and the sensor 28 detects reflected radiation 34, such as electrons reflected from the substrate surface at different directions and/or intensities based on the structure (e.g., fin structure, gate structure, epi growth, spacer growth, etc.) of the semiconductor substrate 20. The sensor 28 outputs data corresponding to the inspected semiconductor substrate 20 to one or more image analysis modules as discussed in greater detail below.

Referring now back to FIG. 1, the analysis unit 16 is in electrical communication with the sensor 28. The analysis unit 16 receives the output from the sensor 28 to generate one or more images corresponding to the semiconductor substrate 20. According to at least one exemplary embodiment, the analysis unit 16 generates an initial image of the semiconductor substrate 20 based on the data output from the sensor 28. The initial image includes a digital image comprising a plurality of pixels that show the structure of the inspected semiconductor substrate 20. Each pixel has one or more respective visual parameters. The visual parameters may include, but are not limited to, color, contrast, and brightness. In addition to the initial image, the analysis unit 16 may generate electron data indicating the energy and/or locations of electrons received at one or more regions of the semiconductor substrate 20.

An operator may define one or more target regions of the semiconductor substrate 20. According to at least one exemplary embodiment, the analysis unit 16 may receive an input indicating a target region where one or more defects are expected to exist. For example, the target region may consist of an area surrounding the epi which may include epi defects, e.g., non-merged epi regions, stunted epi growth regions, or partially-merged epi regions.

The reference image module 18 is in electrical communication with the analysis unit 16 to receive the electron data, the defect data, and/or the target region. Based on the electron data and the defect data, the reference image module 18 may generate a first image (i.e., an initial image) of the inspected semiconductor substrate 20 and may define a target region of the initial image. According to at least one exemplary embodiment, the reference image module 18 may perform a first image processing operation that removes the defects of the initial image indicated by the defect data. The image generated from the first image processing operation may be referred to as a first modified image.

In regard to the target region, the reference image module 18 may further estimate and map a number of electrons corresponding to each pixel included in the target region. The reference image module 18 may then modify the gray-scale level of one or more pixels included in the target region to generate a second modified image that modifies the gray-scale level and enhances the details in the target region of the first modified image. According to an embodiment, the more the electrons, the lighter the gray-scale value and vice versa. The modified image may be output to analysis unit 16 and stored in memory as a golden reference image to diagnose one or more specimen semiconductor substrates subsequently inspected by the e-beam inspection unit 14. It is appreciated that the gray-scale operation may be applied to the initial image without performing the first image processing operation to determine a number of electrons corresponding to each pixel included in the target region. Instead, the gray-scale level of one or more pixels included in the target region may be modified according to a preset gray-scale value regardless of the number of electrons corresponding to each pixel. In this manner, the gray-scale level of all pixels in the target area is modified according to the same preset gray-scale value.

Figure 3:
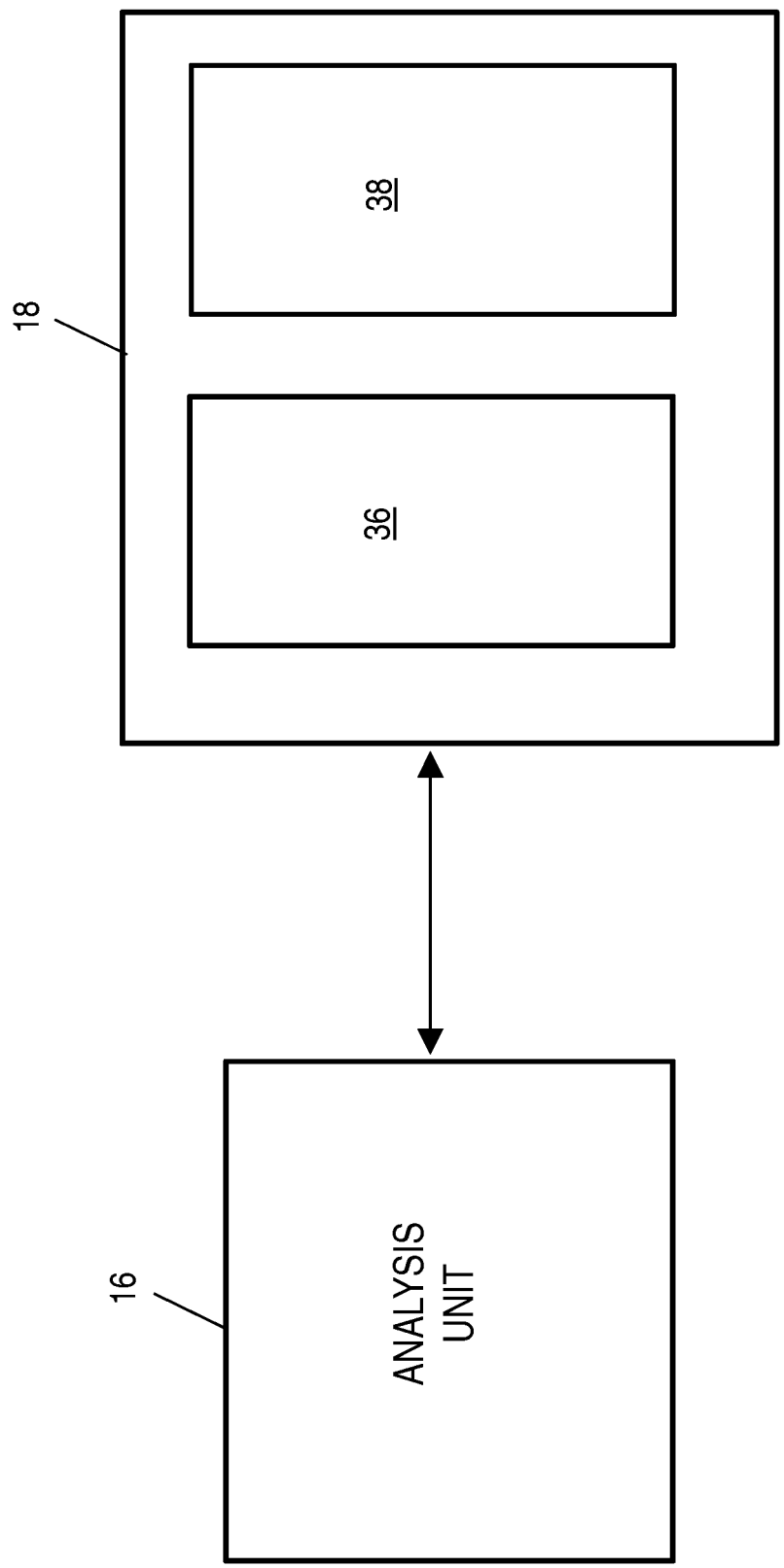
FIG. 3 is a block diagram of a reference image module according to at least one exemplary embodiment.

Turning now to FIG. 3, an electronic reference image module 18 is illustrated according to at least one exemplary embodiment. The reference image module 18 includes an electronic image generator 36 and electronic gray-scale unit 38. The image module 18 may receive electron data and defect data from the analysis unit 16, and may generate a first image (i.e., an initial image) of the inspected semiconductor substrate 20. The image generator 36 may then define a target region of the initial image based on target region data received by the analysis unit 16. The image generator 36 may further determine a number of electrons ($N_1$-$N_n$) corresponding to each pixel included in the target region.

Figure 4:
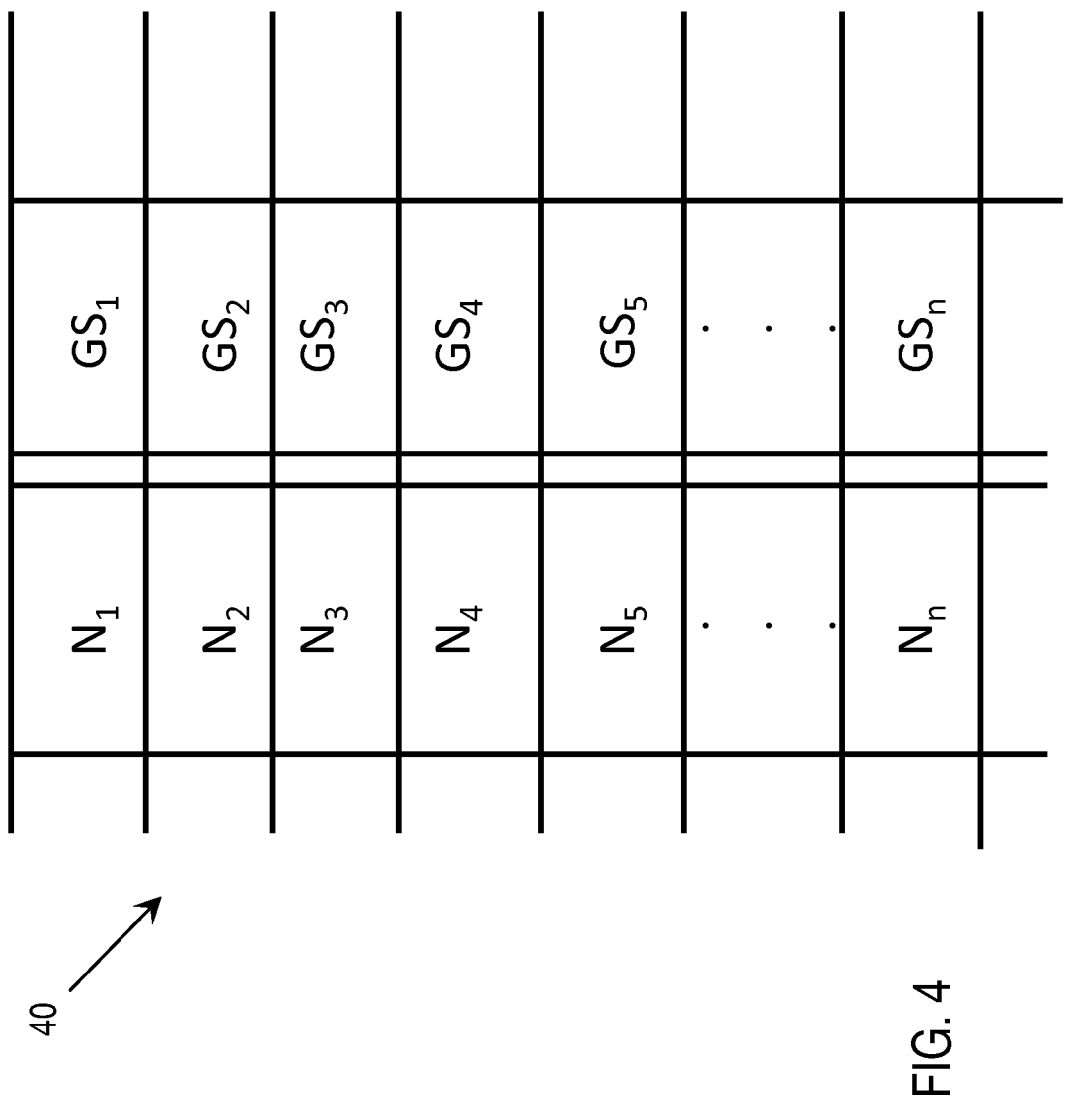
FIG. 4 illustrates a lookup table that cross-references a plurality of electron values with a corresponding a gray-scale value utilized by a reference image module according to at least one exemplary embodiment.

The gray-scale unit 38 includes a memory storing one or more gray-scale lookup tables (LUTs). For example, the gray-scale unit 38 may store a first LUT 40 that includes a plurality of indexed electron number values ($N_1$-$N_n$) cross-referenced to a respective gray-scale value ($GS_1$-$GS_n$) as illustrated in FIG. 4. Accordingly, the gray-scale unit 38 receives the initial image and electron data indicating a number of electrons corresponding to each pixel of the entire initial image. The gray-scale unit 38 may then determine a number of electrons ($N_1$-$N_n$) of each pixel included in the target region, and a modified gray-scale level based on the corresponding gray-scale value ($GS_1$-$GS_n$) stored in the gray-scale LUT 40. The gray-scale unit 38 may adjust the gray-scale level of each pixel based on the determined gray-scale values ($GS_1$-$GS_n$) to remove detected defects in the target region and generate a golden reference image.

According to at least one exemplary embodiment, the gray-scale level of each pixel may be adjusted by modifying one or more visual parameters of a respective pixel. The visual parameters may include, but are not limited to, color, contrast, and brightness. The golden reference image may be output to analysis unit 16 and stored in memory.

According to another embodiment, the gray-scale level of each pixel may be set to a gray-scale value that corresponds to a median gray-scale value. The median gray-scale value may be based on, for example, a median number of electrons included in the target region. Although a median gray-scale value is described, it is appreciated that other values may be used. For example, each pixel of the target region may be set to a value that is a percentage of a gray-scale range.

Figure 5:
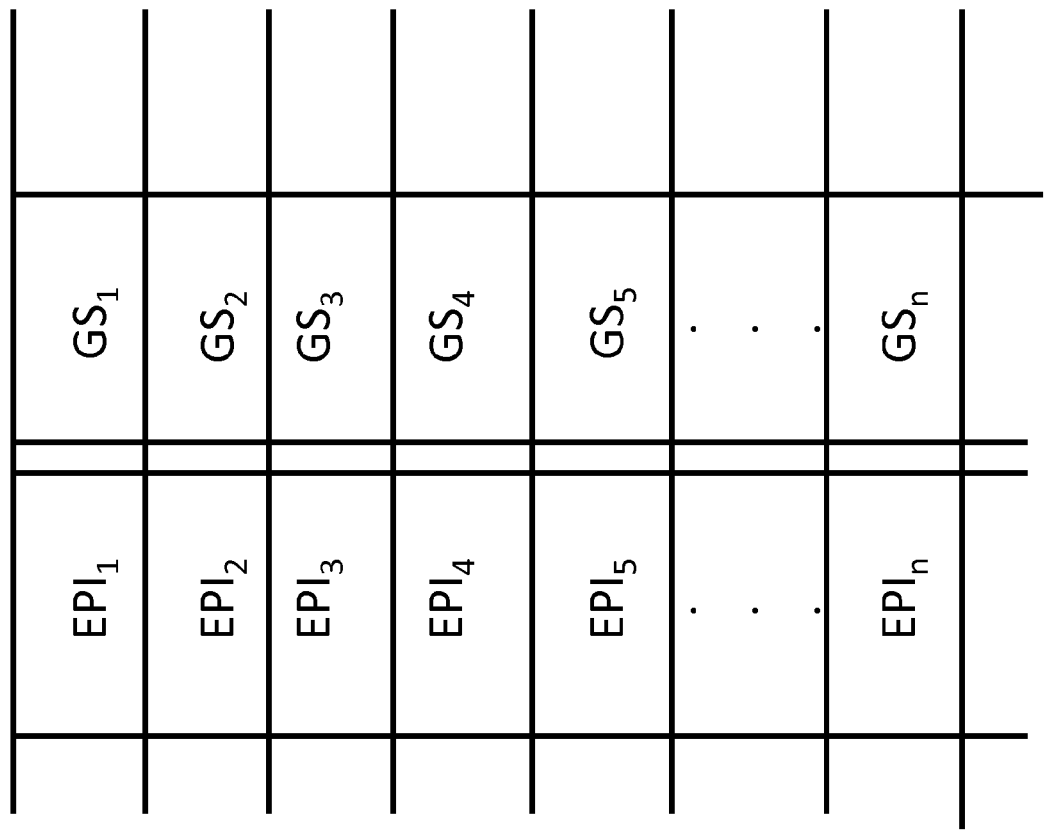
FIG. 5 illustrates another lookup table that cross-references a plurality of epitaxial material thickness values with a corresponding gray-scale value utilized by a reference image module according to at least one exemplary embodiment.

According to still another exemplary embodiment, the gray-scale level of one or more pixels may be adjusted based on a thickness of epi material grown in the target region. More specifically, the reflected radiation 34 detected by the sensor 28 may vary according to the thickness of the epi grown in the target region. The analysis unit 16 may determine the thickness of the epi based on the epi data provided by a film thickness measurement tool. The gray-scale unit 38 may store a second LUT 42 that includes a plurality of indexed epi thicknesses ($EPI_1$-$EPI_n$) cross-referenced to a respective gray-scale value ($GS_1$-$GS_n$) as illustrated in FIG. 5. The gray-scale unit 38 may then receive data from the analysis indicating the thickness of the epi, select a modified gray-scale level based on the corresponding gray-scale value ($GS_1$-$GS_n$)

stored in the second LUT 42, and adjust the gray-scale level of each pixel based on the determined gray-scale values ($GS_1$-$GS_n$) to generate a golden image.

Figure 6:
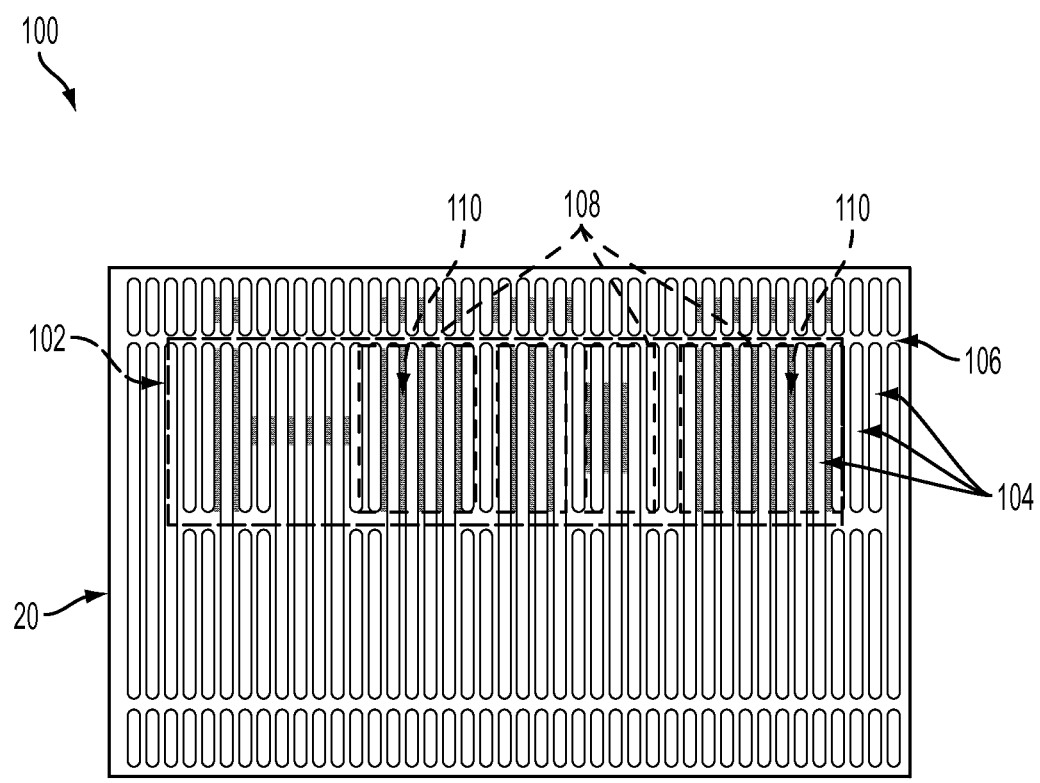
FIG. 6 illustrates an initial image generated by a semiconductor inspection system showing a substrate including a plurality of fins and epitaxially grown material including defects according to at least one exemplary embodiment.

An example of an initial image 100 generated by the reference image module 18 is shown in FIG. 6. The initial image 100 shows an inspected semiconductor substrate 20 including, for example, a pFET region. The pFET region 102 includes a plurality of semiconductor fins 104 and corresponding gate stacks 106.

Figure 7:
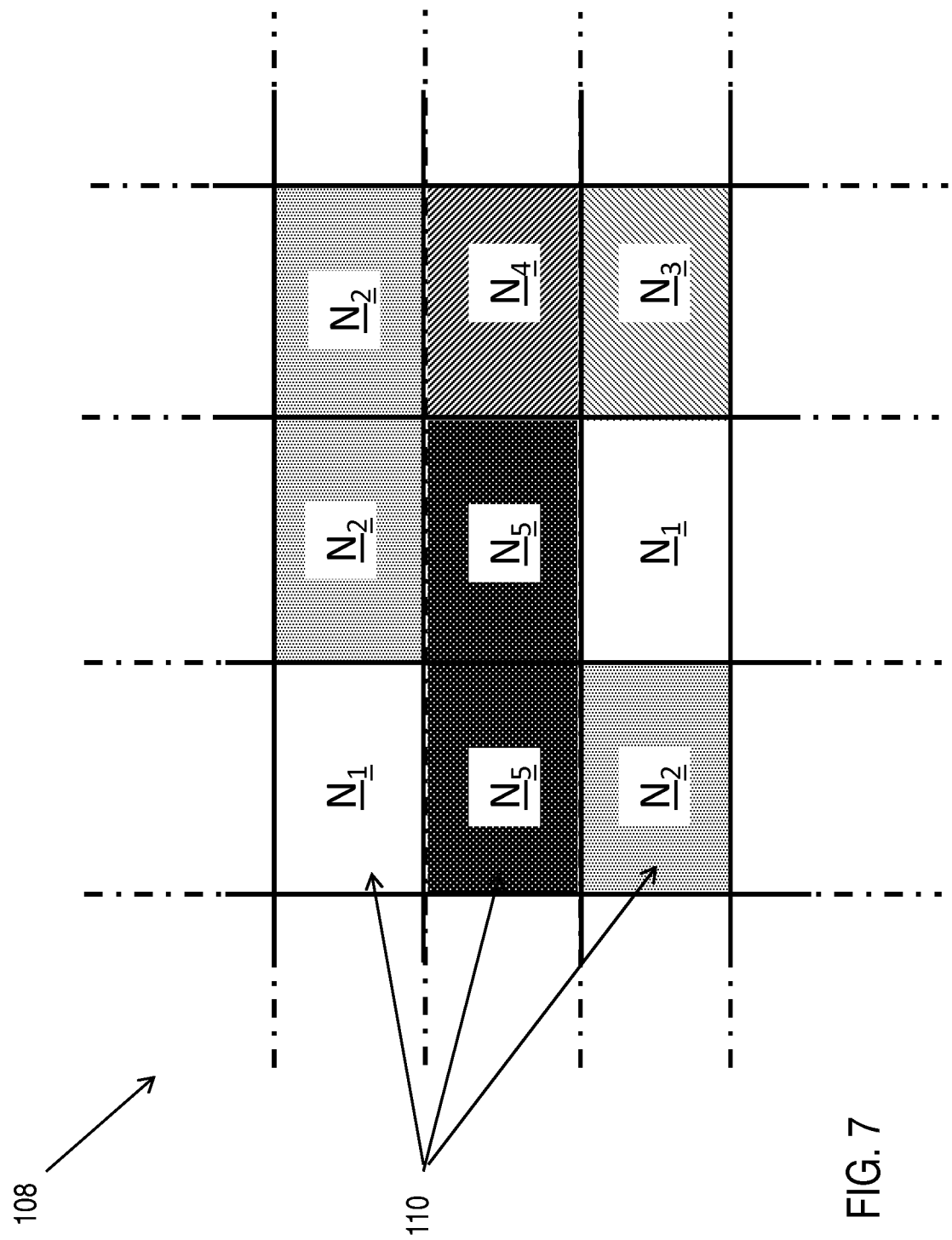
FIG. 7 is a magnified view of the initial image illustrated in FIG. 6 and shows pixels having a number of electrons included in a target region of the initial image.

Referring to FIG. 7, a magnified view of the initial image shown in FIG. 6 is illustrated. The initial image 100 further includes target regions 108 defined by input data received by the analysis unit 16. The target regions 108 may be automatically designated by the analysis unit 16, or may be manually designated via data input to the analysis unit 16 by a user operating the semiconductor inspection system 10. The target regions 108 include, for example, epi grown material having one or more epi defects 110. As described above, the initial image 100 includes a plurality of pixels 110. Each pixel 110 includes a number of electrons ($N_1$-$N_n$). The image generator 36 may determine the number of electrons ($N_1$-$N_n$) corresponding to each pixel included in the target region as discussed in greater detail below.

Figure 8:
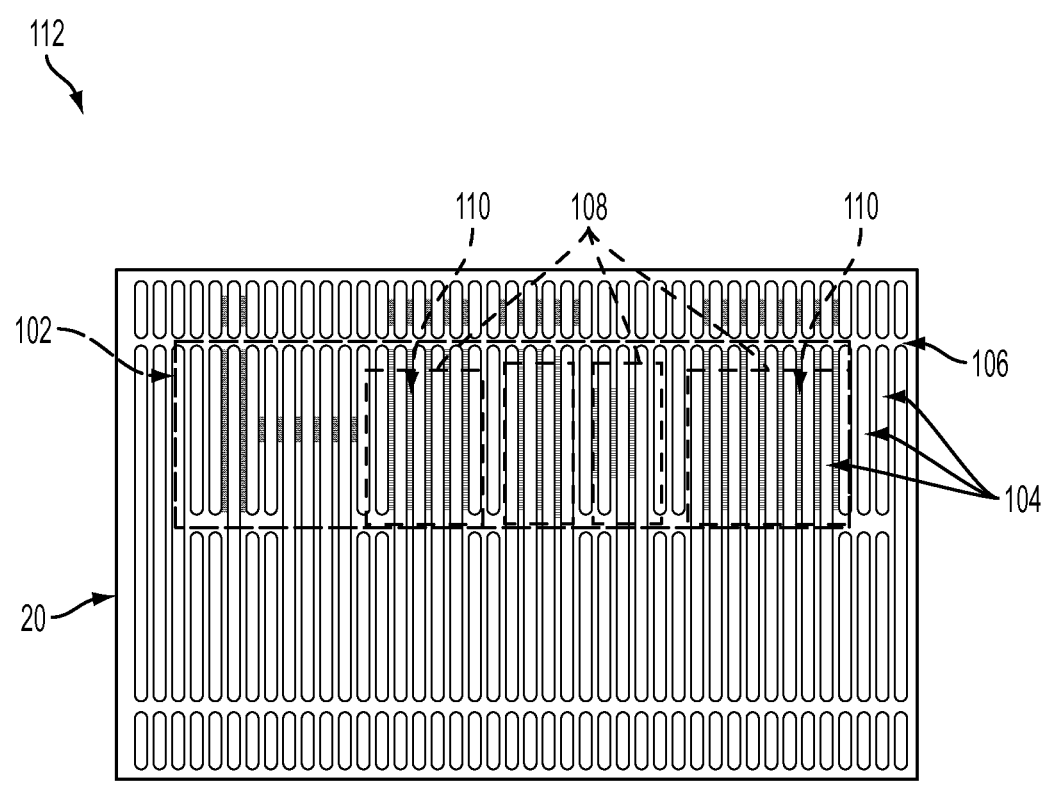
FIG. 8 illustrates the image of FIG. 6 following a first image processing operation that removes the defects from a target region of the initial image to generate a modified image.

Turning to FIG. 8, a modified image 112 generated by the reference image module 18 is shown. The modified image 112 is generated following a first image processing operation that removes the epi defects shown in FIG. 4. Accordingly, the image uniformity of the region located between the semiconductor fins, for example, may be increased.

Figure 9:
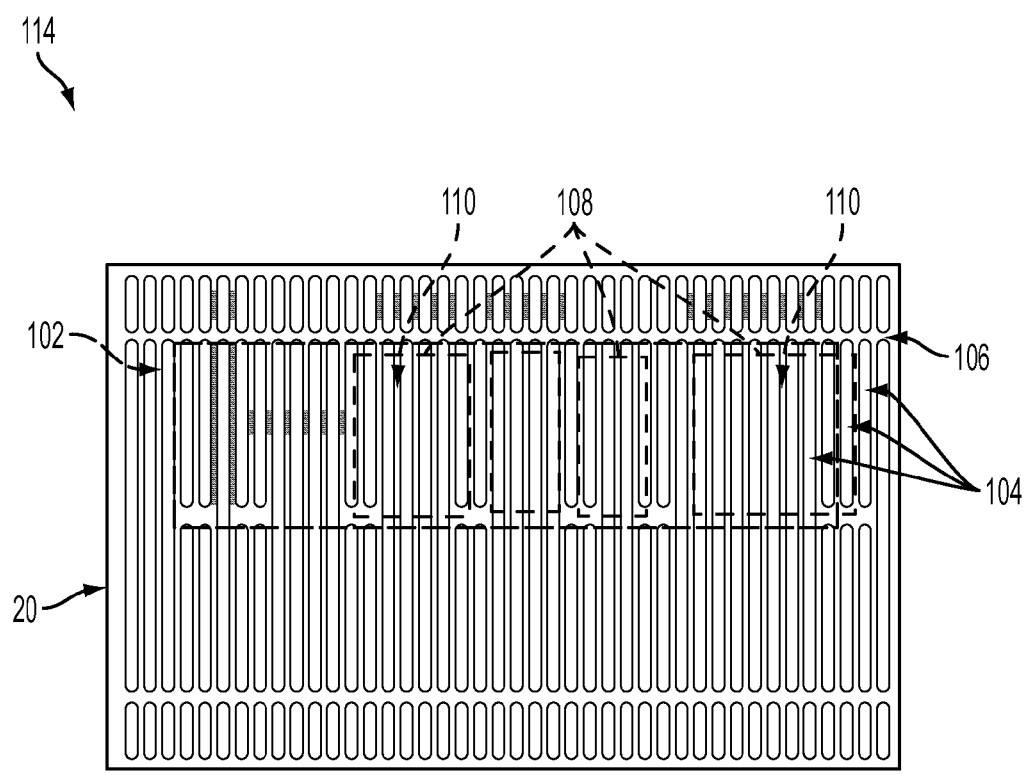
FIG. 9 illustrates the modified image of FIG. 8 following a second image processing operation that adjusts a gray-scale level of the pixels included in the target region to generate a golden image.

Turning now to FIG. 9, a golden image 114 generated by the reference image module 18 is shown. The golden image 114 is generated following a second processing operation that adjusts the gray-scale level of one or more pixels 110 included in the target 108. Accordingly, an enhanced image excluding defects in the target region may be generated and used to determine the quality of specimen semiconductor substrates during subsequent inspections. According to an embodiment, a new golden image is generated for each die.

Figure 10:
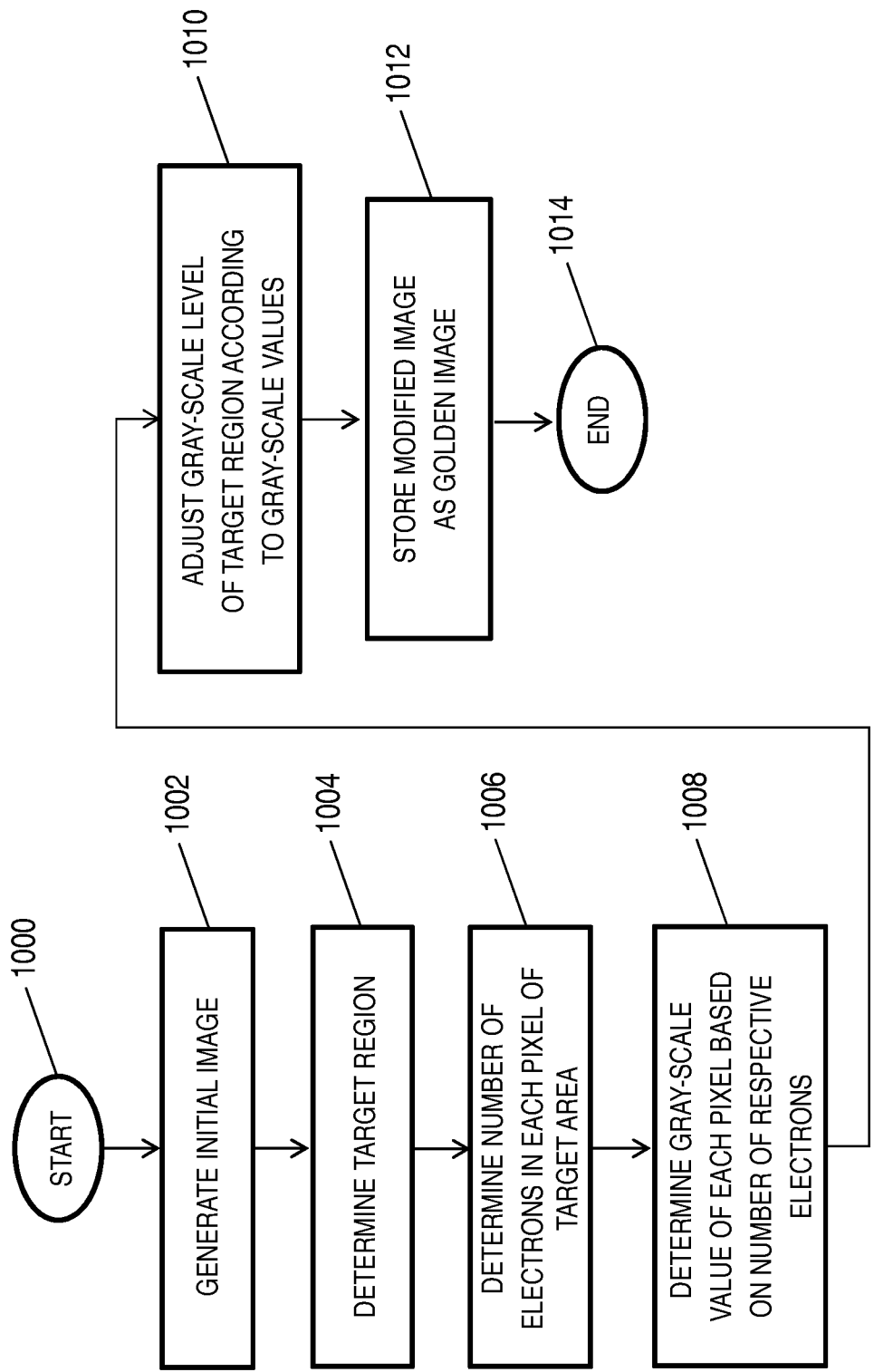
FIG. 10 is a flow diagram illustrating a method of inspecting a semiconductor substrate according to an exemplary embodiment.

Referring to FIG. 10, a flow diagram illustrates a method of inspecting a semiconductor substrate according to an exemplary embodiment. The method begins at operation 1000, and proceeds to generate an initial image of the semiconductor substrate at operation 1002. At operation 1004, a target region of the semiconductor substrate is determined. According to an embodiment, the target region is determined during an inspection operation. At operation 1006, a number of electrons corresponding to each pixel of the initial image is estimated. At operation 1008, a gray-scale value of each pixel is assigned based on a number of respective electrons of the respective pixel. At operation 1010, the gray-scale level of the target region is modified to a single gray scale value. According to an embodiment, operations 1006-1010 happen when inspecting each new wafer. At operation 1012, the modified image included the adjust gray-scale level of the target area is stored as a golden image, and the method ends at operation 1014.

Figure 11:
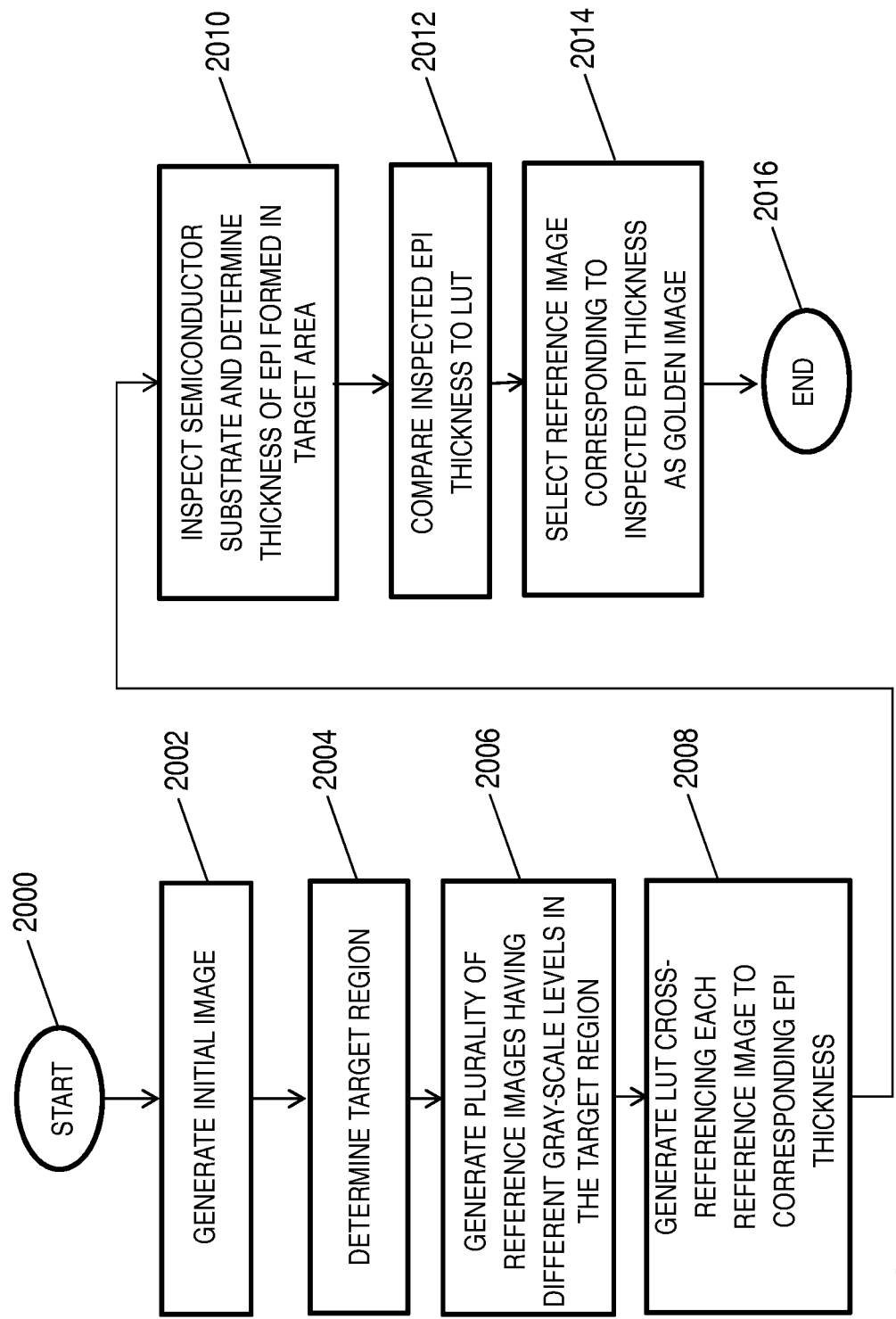
FIG. 11 is a flow diagram illustrating a method of inspecting a semiconductor substrate according to another exemplary embodiment.

Referring to FIG. 11, a flow diagram illustrates a method of inspecting a semiconductor substrate according to another exemplary embodiment. The method begins at operation 2000, and proceeds to generate an initial image of the semiconductor substrate at operation 2002. At operation 2004, a target region of the semiconductor substrate is determined. At operation 2006, a plurality of reference images based on the initial image is generated. Multiple wafers with different film thicknesses are used to generate these multiple images. The target regions will all contain the same number of pixels but the grayscale, which is a function of the film thickness will be different. At operation 2008, a look-up table (LUT) is generated. The LUT includes a plurality of thickness values indicating a thickness of epitaxial grown material included the target region. Each thickness value is cross-referenced with a respective gray-scale value to adjust a gray-scale level of the target region. At operation 2010, a specimen semiconductor substrate is loaded and a thickness of epitaxial material included in the target region is determined. At operation 2012, the determined thickness of the inspected epitaxial material is compared to LUT 42. At operation 2014, a reference image among the plurality of generated reference images is selected according to the LUT. Next the wafer is inspected using the reference image selected 2014. The method ends at operation 2016. According to an embodiment, an inspection operation using this golden reference image as described above may be executed after the method ends at operation 2016.

Figure 12:
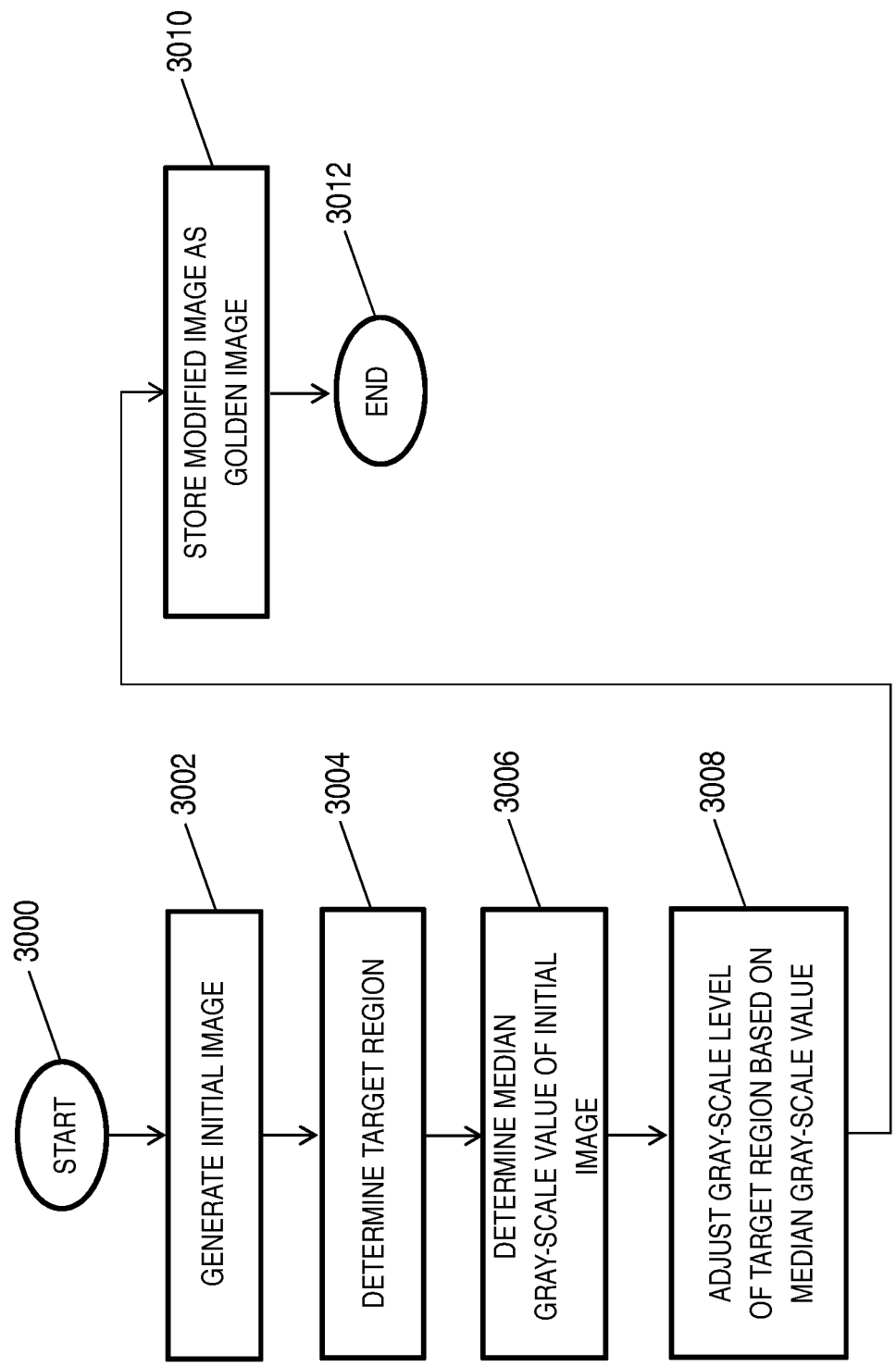
FIG. 12 is a flow diagram illustrating a method of inspecting a semiconductor substrate according to still another exemplary embodiment.

Referring to FIG. 12, a flow diagram illustrates a method of inspecting a semiconductor substrate according to another exemplary embodiment. The method begins at operation 3000, and proceeds to generate an initial image of the semiconductor substrate at operation 3002. At operation 3004, a target region of the semiconductor substrate is determined. According to an embodiment, the target region is determined during an inspection operation. At operation 3006, a median gray-scale value is determined. The median gray-scale value may be a median-gray scale value of the entire initial image, or a median gray-scale value of the target region. As described above, the median gray-scale value may be based on, for example, a median number of electrons included in the target region. Although a median gray-scale value is described, it is appreciated that other values may be used. For example, each pixel of the target region may be set to a value that is a percentage of a gray-scale range. At operation 3008, the gray-scale level of the target region is adjusted according to the determined median gray-scale value. At operation 3010, the modified image having the adjusted gray-scale is stored as a golden image, and the methods ends at operation 3012. According to an embodiment, operations 3006-3010 occur when inspecting each new wafer.

Figure 13:
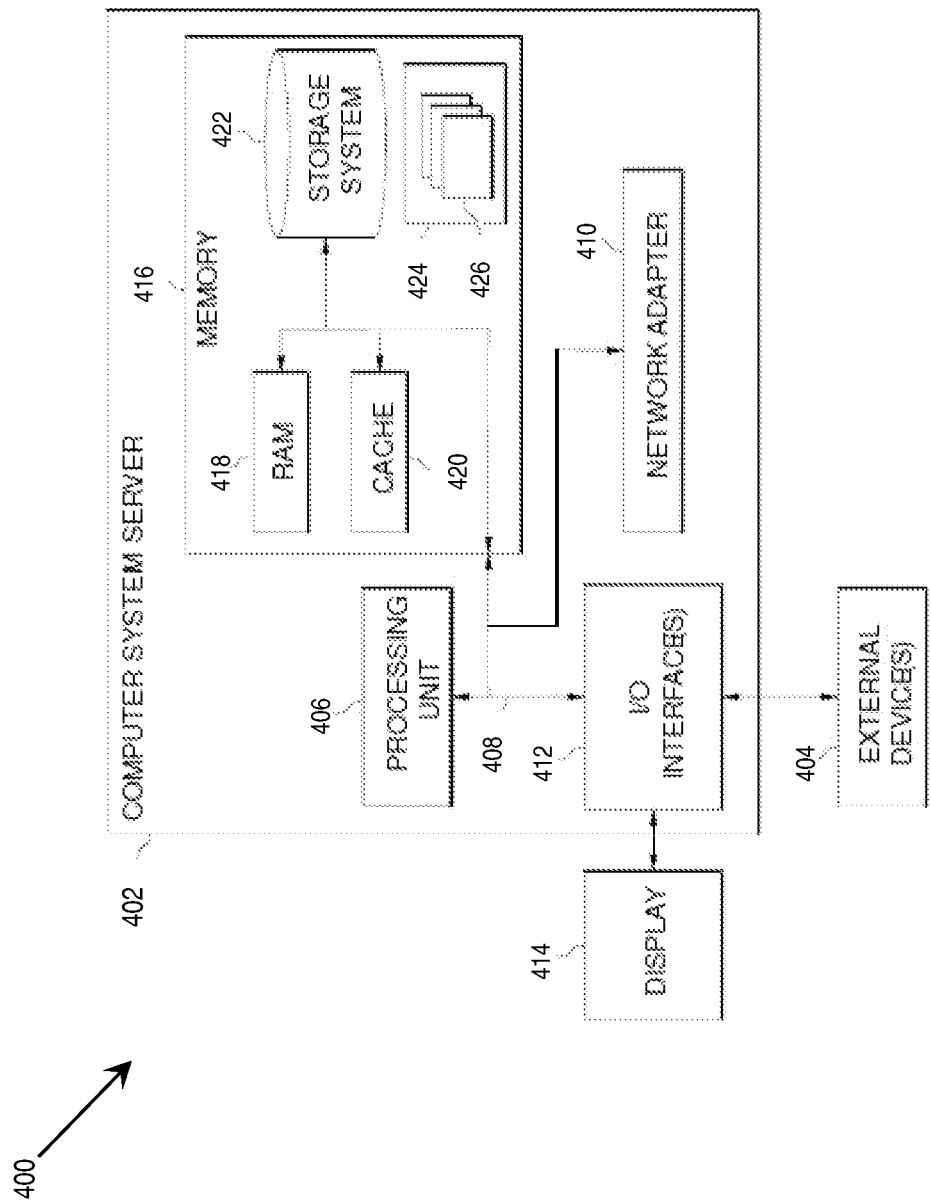
FIG. 13 illustrates a computer system/server included in a computer network according to an exemplary embodiment.

Referring to FIG. 13, a computer system/server included in a computer network is illustrated according to an exemplary embodiment. Regardless, network 400 is capable of being implemented and/or performing any of the functionality set forth hereinabove.

In network 400 there is a computer system/server 402, which is operational with numerous other general purpose or special purpose computing system environments or configurations. Examples of well-known computing systems, environments, and/or configurations that may be suitable for use with computer system/server 402 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 402 may be described in the general context of computer system executable instructions, such as program modules, being executed by a computer system. Generally, program modules may include routines, programs, objects, components, logic, data structures, and so on that perform particular tasks or implement particular abstract data types. Computer system/server 402 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 13, a computer network 400 includes a computer system/server 402 is illustrated according to an exemplary embodiment. The components of computer system/server 402 may include, but are not limited to, one or more processors or processing units 406, a system memory 416, and a bus 408 that couples various system components including system memory 416 to processor 406.

Bus 408 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 402 typically includes a variety of computer system readable media. Such media may be any available media that is accessible by computer system/server 402, and it includes both volatile and non-volatile media, removable and non-removable media.

System memory 416 can include computer system readable media in the form of volatile memory, such as random access memory (RAM) 418 and/or cache memory 420. Computer system/server 402 may further include other removable/non-removable, volatile/non-volatile computer system storage media. By way of example only, storage system 422 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 408 by one or more data media interfaces. As will be further depicted and described below, memory 416 may include at least one program product having a set (e.g., at least one) of program modules that are configured to carry out the functions of embodiments of the invention.

Program/utility 424, having a set (at least one) of program modules 426, may be stored in memory 416 by way of example, and not limitation, as well as an operating system, one or more application programs, other program modules, and program data. Each of the operating system, one or more application programs, other program modules, and program data or some combination thereof, may include an implementation of a networking environment. Program modules 426 generally carry out the functions and/or methodologies of embodiments of the invention as described herein.

Computer system/server 402 may also communicate with one or more external devices 404 such as a keyboard, a pointing device, a display 414, etc.; one or more devices that enable a user to interact with computer system/server 402; and/or any devices (e.g., network card, modem, etc.) that enable computer system/server 402 to communicate with one or more other computing devices. Such communication can occur via Input/Output (I/O) interfaces 412. Still yet, computer system/server 402 can communicate with one or more networks such as a local area network (LAN), a general wide area network (WAN), and/or a public network (e.g., the Internet) via network adapter 410. As depicted, network adapter 410 communicates with the other components of computer system/server 402 via bus 408. It should be understood that although not shown, other hardware and/or software components could be used in conjunction with computer system/server 402. Examples, include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the inventive teachings and the practical application, and to enable others of ordinary skill in the art to understand the invention for various embodiments with various modifications as are suited to the particular use contemplated The flow diagrams depicted herein are just one example. There may be many variations to this diagram or the operations described therein without departing from the spirit of the invention. For instance, the operations may be performed in a differing order or operations may be added, deleted or modified. All of these variations are considered a part of the claimed invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

While various embodiments have been described, it will be understood that those skilled in the art, both now and in the future, may make various modifications which fall within the scope of the claims which follow. These claims should be construed to maintain the proper protection for the invention first described.

What is claimed is:

1. A method of inspecting a semiconductor substrate, the method comprising:
    delivering a beam of electrons to the semiconductor substrate and generating a first image having a plurality of pixels based on electrons emitted from the semiconductor substrate;
    determining a number of electrons emitted by the semiconductor substrate;
    determining at least one target region including at least one defect of the semiconductor substrate; and
    adjusting a gray-scale level of the pixels included in the target region based on the number of received electrons to generate a second image that excludes the at least one defect.

2. The method of claim 1, further comprising comparing the second image to a defect image generated in response to inspecting a specimen semiconductor substrate to determine at least one defect of the specimen semiconductor substrate.

3. The method of claim 2, wherein the adjusting a gray scale further comprises:
    determining at least one gray-scale value based on the number of electrons corresponding to each pixel; and
    mapping the gray-scale value to each pixel included in the target region.

4. The method of claim 3, further comprising generating a look-up table including a plurality of electron values indicating a number of electrons included in a pixel, each electron value cross-referenced with a respective gray-scale value that adjusts a gray-scale level.

5. The method of claim 4, wherein the at least one gray-scale value includes a plurality of gray-scale values, each gray-scale value corresponding to a respective pixel included in the target region.

6. The method of claim 3, wherein the at least one gray-scale value is a median gray-scale value corresponding to the target region.

7. The method of claim 3, wherein a gray-scale level of each pixel included in the target region is adjusted to have a percentile value.

* * * * *